United States Patent
Matias

(10) Patent No.: US 7,332,140 B2
(45) Date of Patent: Feb. 19, 2008

(54) AIR STERILIZATION SYSTEM

(76) Inventor: Carlos J. D. Matias, Rua Mouzinho da Silveira, 27 5C, Lisbon (PT) 1250-166

( * ) Notice: Subject to any disclaimer, the term of this patent is extended or adjusted under 35 U.S.C. 154(b) by 263 days.

(21) Appl. No.: 10/271,444

(22) Filed: Oct. 16, 2002

(65) Prior Publication Data

US 2003/0072688 A1    Apr. 17, 2003

Related U.S. Application Data

(60) Provisional application No. 60/330,048, filed on Oct. 17, 2001, provisional application No. 60/330,050, filed on Oct. 17, 2001.

(51) Int. Cl.
*A61L 9/16* (2006.01)
(52) U.S. Cl. .................. 422/307; 422/4; 392/465; 392/480
(58) Field of Classification Search .............. 422/4, 422/5, 120, 307; 62/78, 531; 392/465, 466, 392/494
See application file for complete search history.

(56) References Cited

U.S. PATENT DOCUMENTS

| | | | | |
|---|---|---|---|---|
| 3,654,432 A | * | 4/1972 | Dyre | 392/492 |
| 3,858,645 A | * | 1/1975 | Egger | 165/66 |
| RE29,932 E | * | 3/1979 | Norback | |
| 4,877,990 A | * | 10/1989 | Fiorenzano, Jr. | 392/465 |
| 5,117,482 A | * | 5/1992 | Hauber | 392/492 |
| 5,347,820 A | * | 9/1994 | In Gweon | 62/78 |
| 5,441,710 A | * | 8/1995 | Marois | 422/307 |
| 5,874,050 A | * | 2/1999 | Matias | 422/120 |
| 6,488,900 B1 | * | 12/2002 | Call et al. | 422/173 |

FOREIGN PATENT DOCUMENTS

| JP | 11276561 A | * | 10/1999 |
|---|---|---|---|
| WO | WO9602281 A1 | * | 2/1996 |

\* cited by examiner

*Primary Examiner*—E. Leigh McKane
(74) *Attorney, Agent, or Firm*—William J. Sapone; Colemane Sudol Sapone P.C.

(57) ABSTRACT

An improved air sterilization system has unobstructed air passageways from a chamber substantially enclosing a volume of air to the air sterilization assembly unit in which the air sterilization assembly unit has heating elements located within air passageways in the unit to exterminate airborne micro-organisms by applying heat to the continuously flowing airstream, and in which the temperature of air leaving the system is insignificantly higher than the temperature of air entering the system.

10 Claims, 5 Drawing Sheets

AIR STERILIZATION SYSTEM

This invention is based upon provisional patent application No. 60/330,048, entitled Refrigerator Air Sterilization Device, filed 17 Oct. 2001; and provisional patent application No. 60/330,050, entitled Room Air Sterilization Device, filed 17 Oct. 2001. The priority date for these provisional patent applications is claimed herein.

BACKGROUND OF THE INVENTION

Since the beginning of the refrigeration industry there have been improvements in the preservation of food products and other heat sensitive products. However, the refrigeration systems utilized do not inhibit the formation of fungi and bacteria inside the refrigerators and other cooling chambers. More recently, some refrigerators have presented new interior air circulation systems that improve the refrigeration of food products by maintaining a constant flow of cold air of essentially constant temperature which keeps foods at a desired constant temperature. These systems, however, have the drawback of increasing the incidence of cross contamination between food items when bacteria and spores are transported by air from one food item to another throughout the entire refrigeration chamber.

Accordingly, there is a need for an improved air sterilization system which can be utilized with existing and new refrigerators with enhanced airflow and temperature technologies so that bacteria, spores, fungi and smells are reduced without negatively impacting the temperature control quality of the refrigeration or other cooling systems.

SUMMARY OF THE INVENTION

The invention is generally directed to an improved air sterilization system for refrigerators, multipurpose chambers, and compartments where it is desired that the sterilization system will not significantly affect the air temperature where the air within the chamber is substantially confined. The system may include an air sterilization assembly that is located wholly within the interior of a chamber, or may be attached to the exterior or may have some components located in the interior while others are located outside of the chamber. The system has at least one air sterilization assembly, at least one air entrance and at least one air exhaust. The air entrance and exhaust are located within the interior of the chamber such that interior air will freely enter and exhaust the air sterilization assembly by means of air convection. The unsterilized air enters the assembly, is cleaned, and the sterilized air is returned to the chamber without significantly altering the inside temperature of the chamber.

The invention uses intense heat contained within capillaries to effectively kill micro-organisms such as mold, bacteria, and virus. Because the device operates without the release of large quantities of heat into the environment, it is particularly suited for use as part of an air sterilization system for a refrigerator, room, multi purpose chamber or compartment requiring air purification. When used inside a refrigeration chamber, the air sterilization system will reduce the development of smells, bacteria, spores and fungi inside the chamber to preserve and extend the shelf life of food products and stored materials.

The air sterilisation device consists of a ceramic core having at least one tube, with at least 2 longitudinal capillaries extending the length of the tube. The capillaries have a diameter between 1 mm and 8 mm and the tube may extend between about 120 mm and 2400 mm in length. In the preferred embodiment, the capillaries are heated with an electrically resistant wire that runs the length of the capillaries. The wire is connected to a power supply. When power runs through the wire, the resistance of the wire generates heat, which is radiated into the air surrounding the wire inside the capillary. The resistant wire is designed to produce heat inside each capillary in excess of 160° Celsius. The heat inside the capillaries generates an upward air stream by heating the air when the ceramic pipe is in a vertical position. The heated air exiting from the upper ends of the capillaries creates a negative pressure at the lower ends of the capillaries which sucks exterior air into the ceramic capillaries and sustains a continuous air circulation through the capillaries. Airborne micro-organisms are exterminated by heat as they pass through the heated capillaries. The continuous airflow generated by air convection assures substantial air sterilisation in a quiet and efficient way and with low power consumption. In the preferred embodiment, the tubes are made of a good quality ceramic or equivalent material that can withstand heat greater then 200° C., and that allows the capillaries to be situated closely together where heat may be exchanged between them. The ceramic core is located within an exterior casing having an air access opening at the bottom. An optional heat exchanger can be used at some distance above the ceramic capillaries, and may have a casing top that is resistant to impact and heat, and that has at least one air outlet that will boost airflow out of the device. In the preferred embodiment, the casing will incorporate the ceramic core and be attached to a wall.

Accordingly, it is an object of the invention to reduce airborne micro-organisms and of avoid the formation of smells, fungi, mold and bacteria in food-containing air chambers.

It is a second object of the invention to provide an improved sterilization system for refrigerators, incorporating air sterilization assemblies.

Another object of the invention is to provide an improved air sterilization system for refrigerators in which air sterilization assemblies including intake and outlet connections pass air in the refrigerator through the air sterilization assembly which kills fungus, bacteria and other airborne micro-organisms through heat.

Still a further object of the invention is to provide an improved air sterilization system for refrigerators which utilizes a fan to enhance the air flow through the air sterilizing assembly.

Yet still a further object of the invention is to provide an improved air sterilization system in which the air sterilization assembly is coupled to a cooling chamber so that the air from the cooling chamber passes through the sterilization system where the heat inside is used to kill the micro-organisms and the heat does not adversely affect the internal temperature of the cooling chamber.

Still another object of the invention is to provide an improved air sterilization system in which the air assembly is coupled to a multi purpose chamber or room for sterilizing the air.

Yet another object of the invention is to provide an improved air sterilization system to be attached to automobiles, trains, subway cars, submarines, aircraft, cruise ships, war vessels and other types of vehicles in which the air in a restricted volume is to be purified.

Still other objects and advantages of the invention will be apparent from the following description of the preferred embodiments.

The invention accordingly comprises the features of construction, combination of elements, arrangement of parts, combination of steps and procedures, all of which will be exemplified in the constructions and processes hereinafter set forth and the scope of the invention will be indicated in the claims.

BRIEF DESCRIPTION OF THE DRAWINGS

For a fuller understanding of the invention, reference is made to the following description taken in connection with the accompanying drawings, in which.

DETAILED DESCRIPTION OF THE PREFERRED EMBODIMENTS

Figure 1:
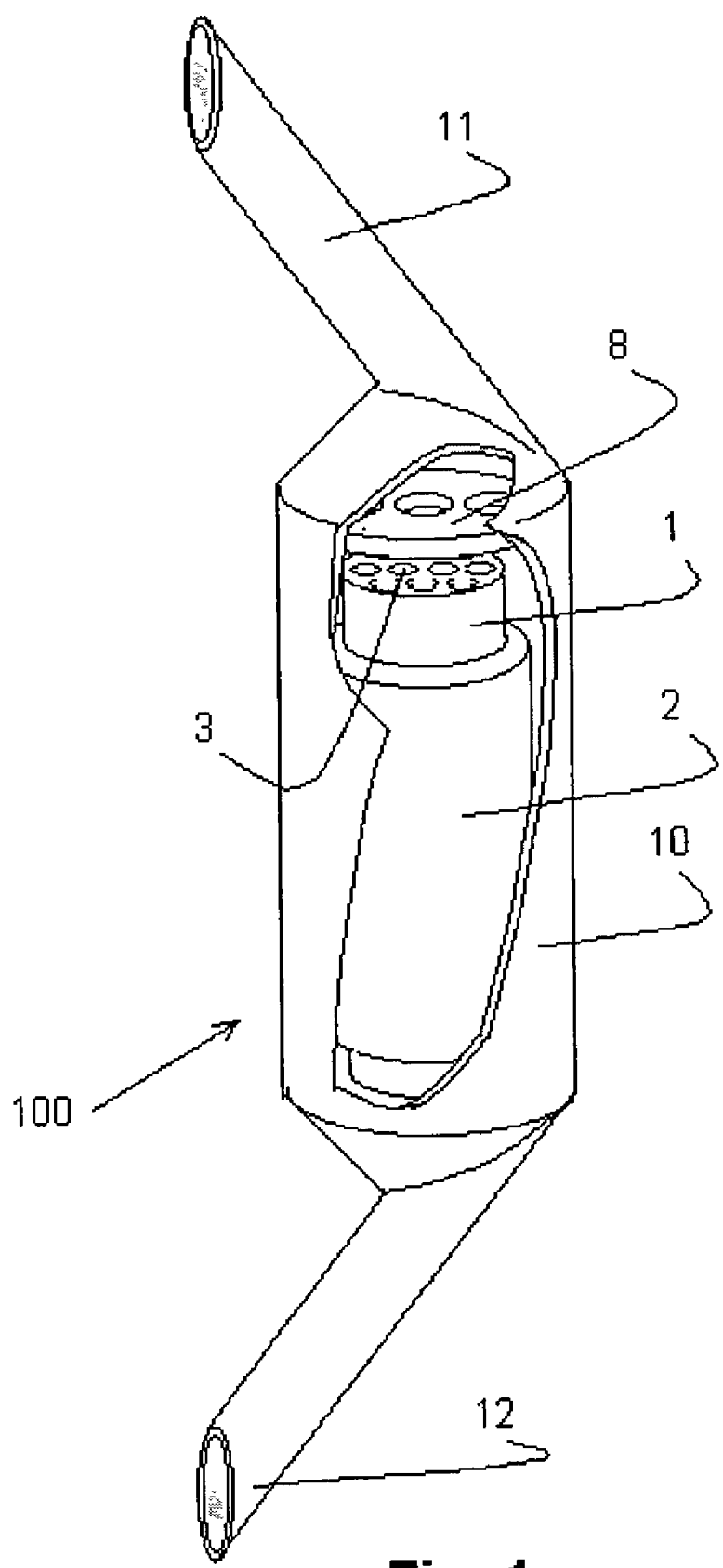
FIG. 1 is a cutaway perspective view of an air sterilization assembly constructed in accordance with a preferred embodiment of the invention.

Reference is first made to FIG. 1 in which an air sterilizing assembly, generally indicated as 100, constructed in accordance with a preferred embodiment of the invention, is depicted. Air sterilizer assembly 100 has contaminated air entering by air convection at inlet 12. The air in sequence enters the sterilizing ceramic element 1 of the type shown and described in Applicant's prior U.S. Pat. No. 5,874,050, which is inserted in an optional insulated element 2. The hot sterilized air exhausts at the sterilizing element top end 3. The hot sterilized air is then cooled at optional heat exchanger 8. Finally the cooled, sterilized air exhausts air sterilizer chamber 10 through outlet 11 back to the refrigerator or chamber.

Figure 2:
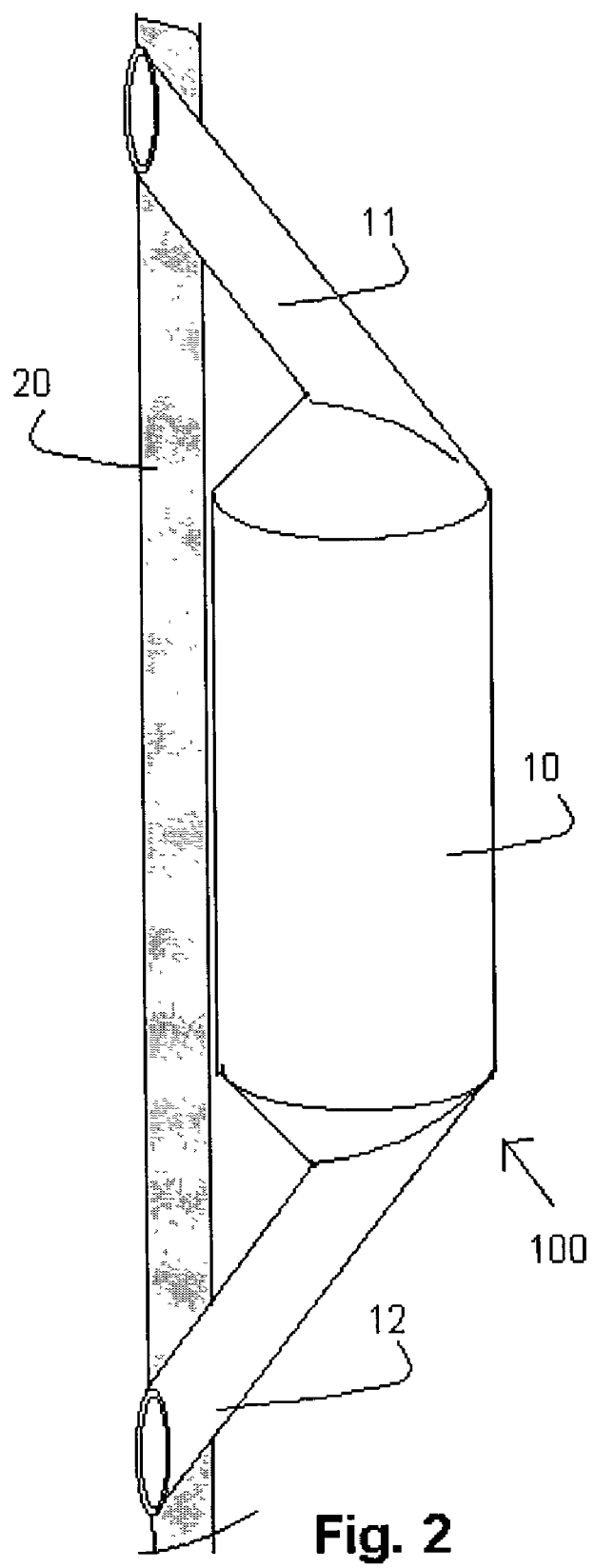
FIG. 2 is a side elevation view of a air sterilizing assembly as in FIG. 1, attached through the wall of a refrigerator.

As shown in FIG. 2, like referenced elements being represented by like referenced numerals, air sterilization assembly 100 is affixed outside of the wall 20 of the chamber. As shown in FIG. 2, the left side of wall 20 is the interior of the chamber compartment. Air inlet 12 is shown open on the inside of the chamber compartment with the flow of air through air sterilization assembly 10 and then back out through exhaust outlet 11 through wall 20 of the chamber. In this way, the heat associated with the sterilization process is applied outside of the chamber wall causing less impact on the interior temperature of the refrigerator.

Figure 3:
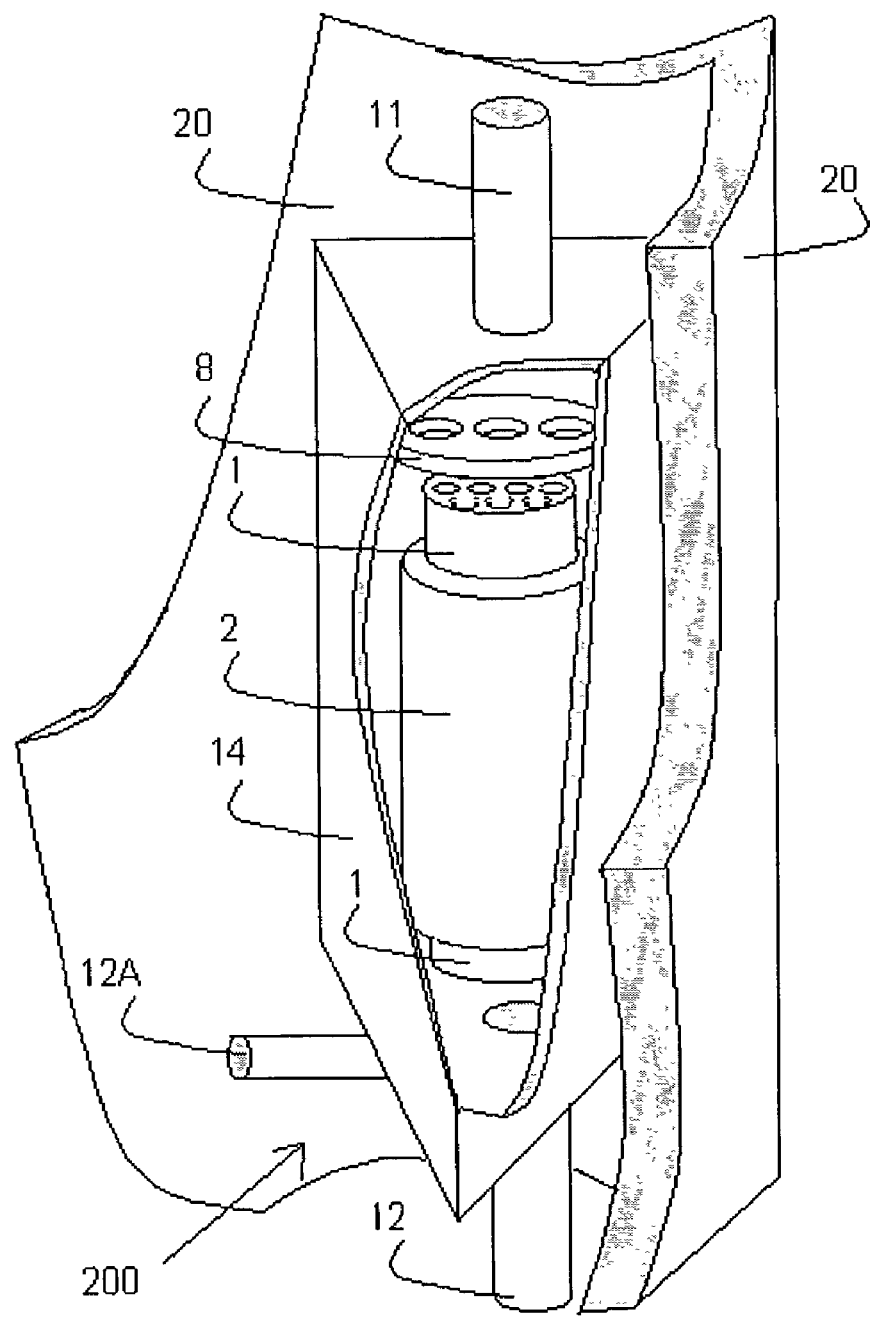
FIG. 3 is a cutaway perspective view of an air sterilization assembly constructed in accordance with a preferred embodiment of the invention in which the air sterilization assembly is inside the refrigerator wall.

Reference is next made to FIG. 3 where air sterilization system 200 with air sterilization assembly 10 (not shown) including ceramic element 1 inserted in optional insulated element 2 and optional heat exchanger 8, all at the inside of the refrigerator corner next to wall 20 is shown. In this case, the air sterilization assembly 10 is placed in an insulated chamber 14 and the air sterilization assembly 10 includes optional contaminated air inputs 12 and 12A and one exhaust 11.

Figure 4:
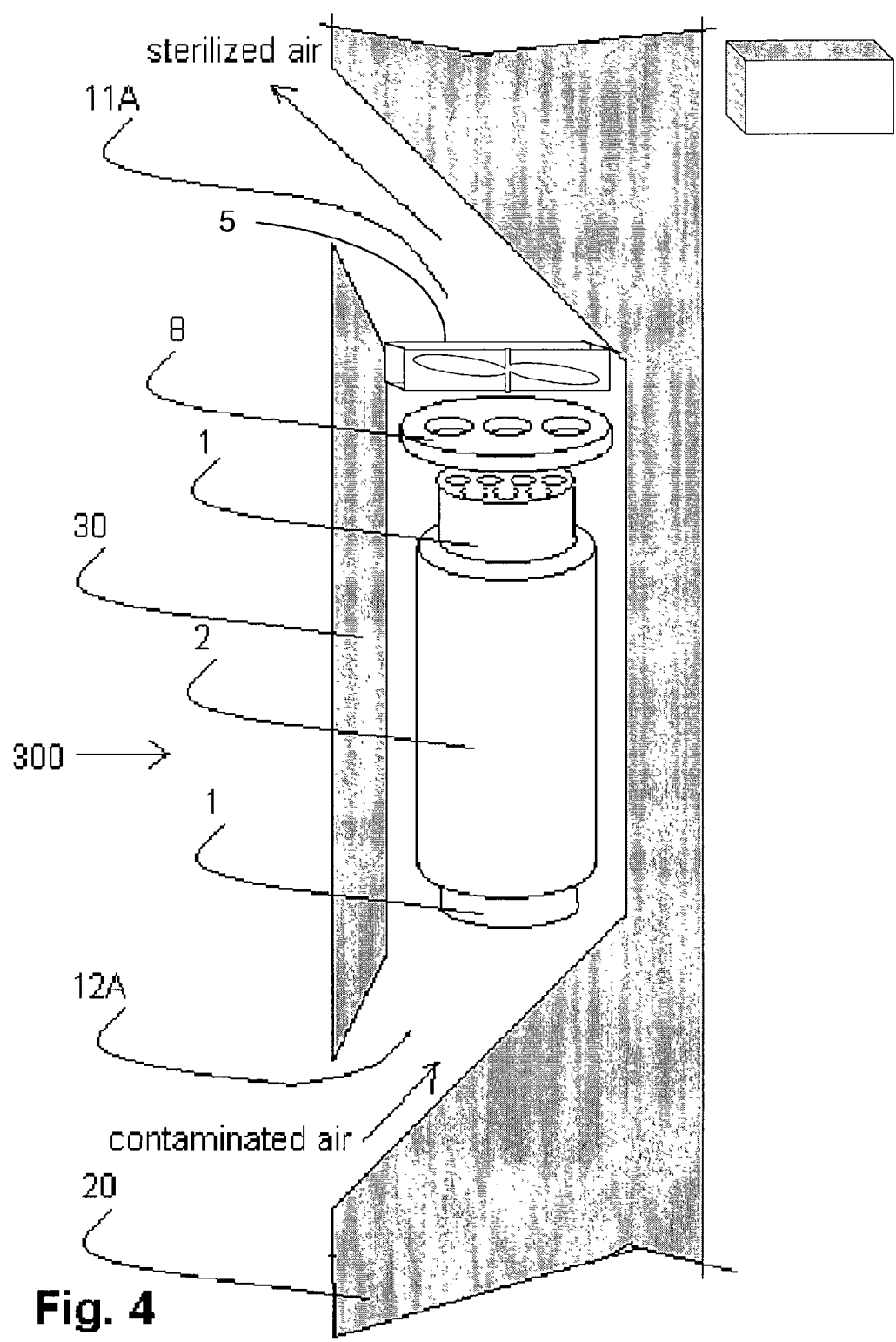
FIG. 4 is a partially cutaway perspective view of an air sterilizing assembly inserted in a wall constructed in accordance with a preferred embodiment of the invention.

Reference is next made to FIG. 4 wherein an air sterilization assembly 300 constructed in accordance with another preferred embodiment of the invention is depicted, like elements being depicted by like referenced numerals. In this case, the air sterilization assembly 300 is placed in a tube 30 in refrigerator wall 20. One portion of channel 30 serves as air inlet 12A and another portion as exhaust outlet 11A. An optional circulation fan 5 is shown in the air channel to assist in improving airflow through the assembly. Although the fan is located above the assembly, its positioning is not critical, and it may be mounted below the sterilization assembly, if desired. The air sterilization assembly 300 again includes an air sterilizing element 1, an insulating element 2 and a heat exchanger 8. Though only a single such sterilizing element 1 is shown, it is possible to have multiple elements of this sort in the same refrigerator.

In each of these embodiments the electrical connections to the air sterilizing units are not shown. These are conventional connections, such as those of the type already shown in Applicant's prior U.S. Pat. No. 5,874,050.

Figure 5:
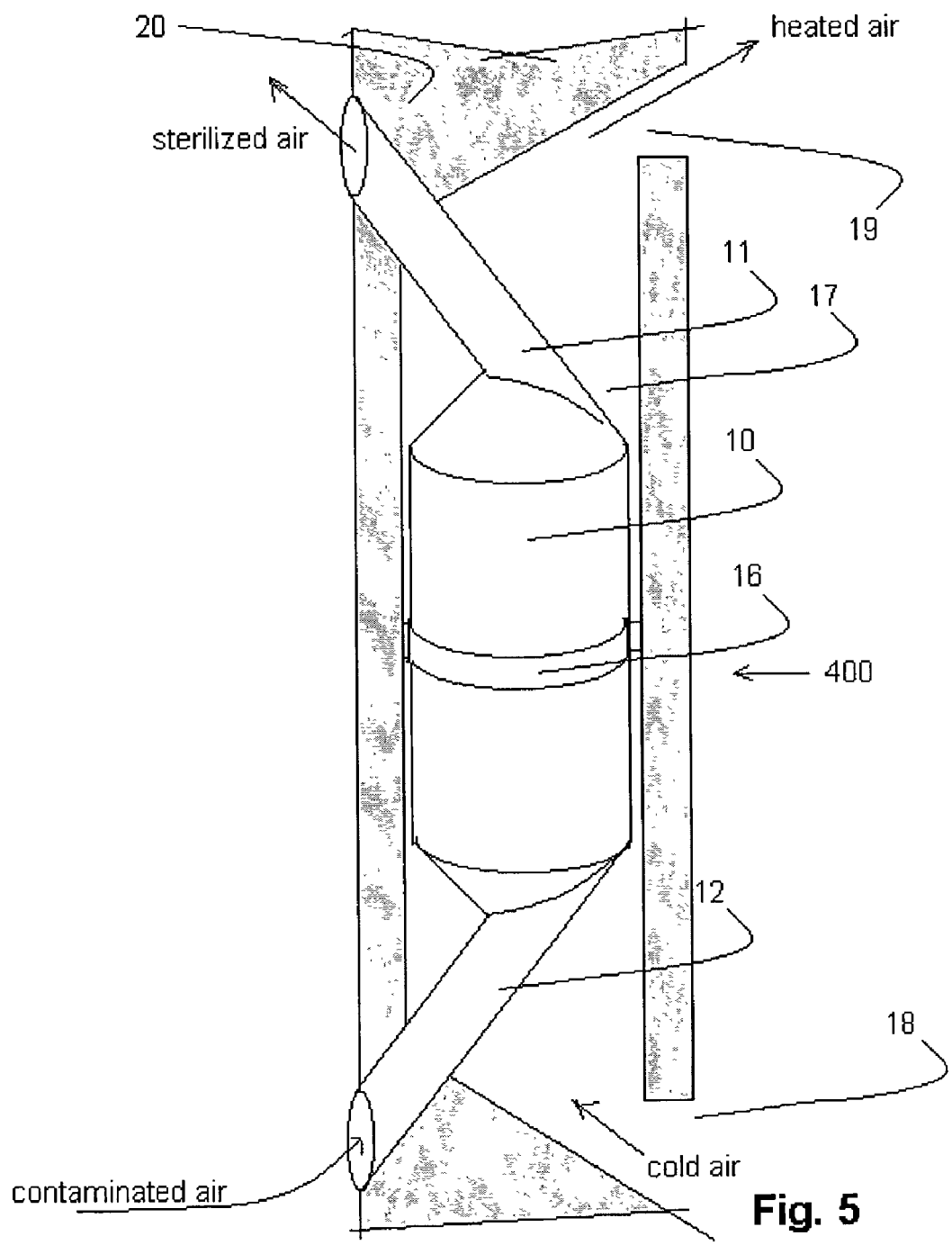
FIG. 5 is a cutaway perspective view of an air sterilization assembly attached to the outside surface of a chamber wall, constructed in accordance with another preferred embodiment of the invention.

Reference is next made to FIG. 5 wherein an air sterilization assembly 400, constructed in accordance with another preferred embodiment of the invention, is depicted. Air sterilization assembly 400 is one in which contaminated air from the inside of a room wall 20 enters inlet 12, passes through sterilization assembly main body 10 and exhausts via outlet 11 back to the room. A cooling chamber 17, receiving cold air from inlet 18 and exhausting via outlet 19 is used to cool the sterilization assembly 400 which in turn will reduce the temperature of the air returning to the inside of the room of side wall 20 so as to minimize the increase in temperature inside the room as a result of the sterilization process. Air sterilization assembly main body 10 is held in place within cooling chamber 17 via attachment means 16 which may be of a conventional nature. The air sterilization assembly 400 may also be held in place by other means.

With the use of the new air sterilization system as shown in the various figures, air circulation through the air sterilization assemblies is created by air convection through the use of air sterilizers similar to those used in room air sterilizer devices invented by Applicant in U.S. Pat. No. 5,874,050. The air sterilization technology utilized offers excellent results with exceptional reduction in micro-organisms and improvement in indoor air quality as proven by international laboratories, including INETI—Laboratory of Microbiology in Lisbon, SGS Natec in Hamburg, Universidad Complutense of Madrid, TMC—Technical Micronics Corporation in the United States of America and other tests. These tests show that the sterilization assembly system operates in a highly improved fashion when compared to systems relying on filters, and chemical agents. No air sterilizing or air purifying systems are available up to today for refrigerators and cooling chambers.

In other preferred embodiments of the invention the refrigerator or chamber or room would be outfitted with one or more sterilization assemblies. Generally, each of the air sterilization assemblies includes at least one air input and at least one air exhaust outlet connected to the interior of the contained volume so that the air inside said contained volume will freely enter and exhaust each air sterilization assembly. The system can operate either with the natural air convection occurrence caused by air heating at the capillaries of the air sterilizing assembly ceramic element or by a dedicated air flow system associated with the air sterilization assembly. The dedicated air flow system may include a fan to blow air into the air sterilization assembly input port or a fan to pull air from the output port.

To minimize the effect of the heat utilized in the air sterilization assembly, the system may include an additional cooling chamber inside or outside of the air sterilization assembly which cools the flow of air coming out of the ceramic core exhaust outlet prior to re-entry into the enclosed air volume such as a chamber, room or refrigerator.

In addition to being utilized in refrigerators, cooling and multipurpose chambers and rooms, the air sterilization assembly can be utilized in enclosed volumes and also in connection with cooling or heating systems such as vehicles as automobiles, trains, subway cars, submarines, aircraft, cruise ships, war vessels and other types of vehicles in which there are enclosed volumes which are either cooled, heated or merely include airflow. In these cases, the size and number and location of the air sterilization assemblies incorporated into the system are adaptable based upon the needs of the system, including its volume, airflow, temperature, humidity and other physical characteristics.

Accordingly, an improved air sterilization assembly capable of sterilizing a refrigerator or other air contained volume is provided. The air sterilization assembly includes input and exhaust outlets with air flowing through a sterilization chamber where the air is heated to a sufficiently high temperature so as to kill micro-organisms and the output air is cooled either through the use of a heat exchanger and/or a cooling chamber. The air sterilization assembly can be placed either fully inside the room, chamber, compartment, refrigerator or inside or outside its side walls and or a partial or total mixture of said options with direct inlet and outlet connections to the room, chamber, compartment, refrigerator or into channels built into their side walls.

It will thus be seen that the objects set forth above, among those made apparent in the proceeding description, are efficiently obtained and, since certain changes may be made in the above constructions and processes without departing from the spirit and scope of the invention, it is intended that all matter contained in the above description or shown in the accompanied drawings shall be interpreted as illustrative, and not in the limiting sense.

It will also be understood that the following Claims are intended to cover all of the generic and specific features of the invention herein described and that all statements of the scope of the invention which, as a matter of language, might be said to fall therebetween.

What is claimed is:

1. A sterilization system for exterminating airborne micro-organisms in an airstream received from a chamber in which a volume of air is substantially enclosed and to which the airstream is to be returned consisting essentially of an air sterilization assembly having:

an air sterilization chamber surrounding one or more air sterilization passageways therein for confining the airstream passing therethrough, the one or more passageways being capillary passageways oriented substantially vertically and extending for at least 120 mm, one or more heating elements situated within said one or more air sterilization passageways, said one or more heating elements being heated to a temperature of not less than 160 degrees Celsius, for radiating heat into said one or more substantially vertical air sterilization passageways, heating the air therein, thereby sterilizing the air;

at least one exhaust air passageway extending from said air sterilization chamber to the chamber in which a volume of air is substantially enclosed and being substantially unobstructed therebetween, the air exhaust passageway disposed on top of the air sterilization chamber, said sterilized heated air flowing up and out of the air exhaust passageway;

at least one entrance air passageway extending from the chamber in which a volume of air is to be sterilized to said air sterilization chamber and being substantially unobstructed therebetween, the air entrance passageway disposed on a bottom of the air sterilization chamber, the flow of sterilized air passing through the air exhaust passageway causing new contaminated air to flow into the air entrance passageway, creating a continuous upward airflow known as air convection;

means for substantially preventing heat from the heating elements from transferring to the chamber in which a volume of air is substantially enclosed;

means for circulating air located external to the chamber in which a volume of air is to be sterilized about external surfaces of the air sterilization chamber, air entrance passageway and exhaust air passageway, to remove heat generated by the air sterilization therefrom;

the one or more air passageways directing a continuous flow therethrough of an airstream received from the chamber in which a volume of air is substantially enclosed such that airborne micro-organisms within said airstream are exposed to the heat radiated from said heated elements and are exterminated thereby, such that a cleaned airstream is returned by air convection to said chamber in which a volume of air is substantially enclosed through the at least one exhaust air passageway, thereby drawing an uncleaned airstream into the at least one entrance air passageway, due to a negative pressure created at an entrance to the one or more passageways, created by the exhaust of sterilized air at the at least one passageway air exhaust and;

said air sterilization assembly only minimally heating the airstream delivered to the chamber in which a volume of air is substantially enclosed.

2. The sterilization system of claim 1 wherein said air sterilization assembly is situated externally to said chamber in which a volume of air is substantially enclosed, the means for substantially preventing heat from the heating elements from transferring to the chamber in which a volume of air is substantially enclosed being a wall disposed therebetween.

3. The sterilization system of claim 1 wherein said air sterilization assembly is situated within one or more walls of said chamber in which a volume of air is substantially enclosed, the means for substantially preventing heat from the heating elements from transferring to the chamber in which a volume of air is substantially enclosed being the wall disposed therebetween.

4. The sterilization system of claim 1 wherein said chamber in which a volume of air is substantially enclosed is a refrigerated chamber.

5. The sterilization system of claim 1 wherein said chamber in which a volume of air is substantially enclosed comprises a plurality of chambers.

6. The sterilization system of claim 1 wherein said chamber in which a volume of air is substantially enclosed is a vehicle compartment.

7. The sterilization system of claim 1 wherein the means for circulating air is a heat exchanger.

8. The sterilization system of claim 7 wherein the heat exchanger cools the cleaned airstream to a temperature that is substantially the same as a temperature of said air entering said entrance air passageway.

9. The sterilization system of claim 1 wherein the means for circulating air comprise a cooling chamber having a cool external air inlet and an air outlet, the air sterilization assembly disposed within the cooling chamber such that the air sterilization assembly is cooled by the external air circulating therethrough.

10. The sterilization system of claim 1 wherein the means for circulating air is a heat exchanger, and the one or more heating elements are insulated elements.

* * * * *